United States Patent [19]

Irmiter et al.

[11] Patent Number: 4,863,452
[45] Date of Patent: Sep. 5, 1989

[54] VENOUS RESERVOIR

[75] Inventors: Richard J. Irmiter, Minneapolis; Larry E. Fuller, Minnetonka; Felix J. Martinez, Plymouth, all of Minn.

[73] Assignee: Minntech Corporation, Minneapolis, Minn.

[21] Appl. No.: 828,951

[22] Filed: Feb. 12, 1986

[51] Int. Cl.$^4$ .............................................. A61M 1/03
[52] U.S. Cl. ..................................... 604/408; 604/122
[58] Field of Search ........................................ 604/4–7, 604/122, 322–323, 408, 410, 262; 128/DIG. 24; 248/95

[56] References Cited

U.S. PATENT DOCUMENTS

| | | |
|---|---|---|
| Re. 32,065 | 1/1986 | Ralston, Jr. et al. |
| 272,762 | 2/1884 | Tanner, II. |
| 3,058,464 | 10/1962 | Broman .......................... 128/DIG. 3 |
| 3,256,883 | 6/1966 | DeWall .............................. 128/400 |
| 3,513,845 | 5/1970 | Chesnut et al. ........................ 604/4 |
| 4,026,669 | 5/1977 | Leonard et al. ..................... 604/122 |
| 4,188,989 | 2/1980 | Andersen. |
| 4,213,561 | 7/1980 | Bayham. |
| 4,396,383 | 8/1983 | Hart. |
| 4,428,743 | 1/1984 | Heck .................................. 604/122 |
| 4,432,763 | 2/1984 | Manschot et al. |
| 4,449,969 | 5/1984 | Schweizer ......................... 604/322 |
| 4,462,510 | 7/1984 | Steer et al. ......................... 604/323 |
| 4,484,920 | 11/1984 | Kaufman et al. |
| 4,493,705 | 1/1985 | Gordon et al. ..................... 604/122 |

OTHER PUBLICATIONS

A SYSTEM APPROACH, a page from Shiley product literature.
CAPIOX II, The Data & Instruction Manual from Terumo Corporation, p. 21, Drawing page 7 from an Instruction and Information Manual from Terumo.
ADVERTISING PAGE from Shiley.
BENTLEY BOS–CM40 and CM50 Capillary Membrane Oxygenators, p. 2 from a Performance Characteristics paper of Bentley.

*Primary Examiner*—C. Fred Rosenbaum
*Attorney, Agent, or Firm*—Vidas & Arrett

[57] ABSTRACT

A venous reservoir for use in cardiotomy bypasses comprising a flexible, variable capacity bag having a vertical seal positioned between the outlets and inlets along the lower seal line. The vertical seal line is positioned off-center such that the velocity of blood decreases as it passes the top of said seal line and towards the lower outlet to increase the removal of bubbles from the blood. All ports serving the reservoir are constructed without internal projections into the reservoir to decrease the possibility of thrombosis. The upper and lower edges of the reservoir are looped to receive horizontal rods slidably attached to a vertical support. Adjustment of the distance between the rods varies the volume possible within the reservoir.

1 Claim, 1 Drawing Sheet

U.S. Patent  Sep. 5, 1989  4,863,452
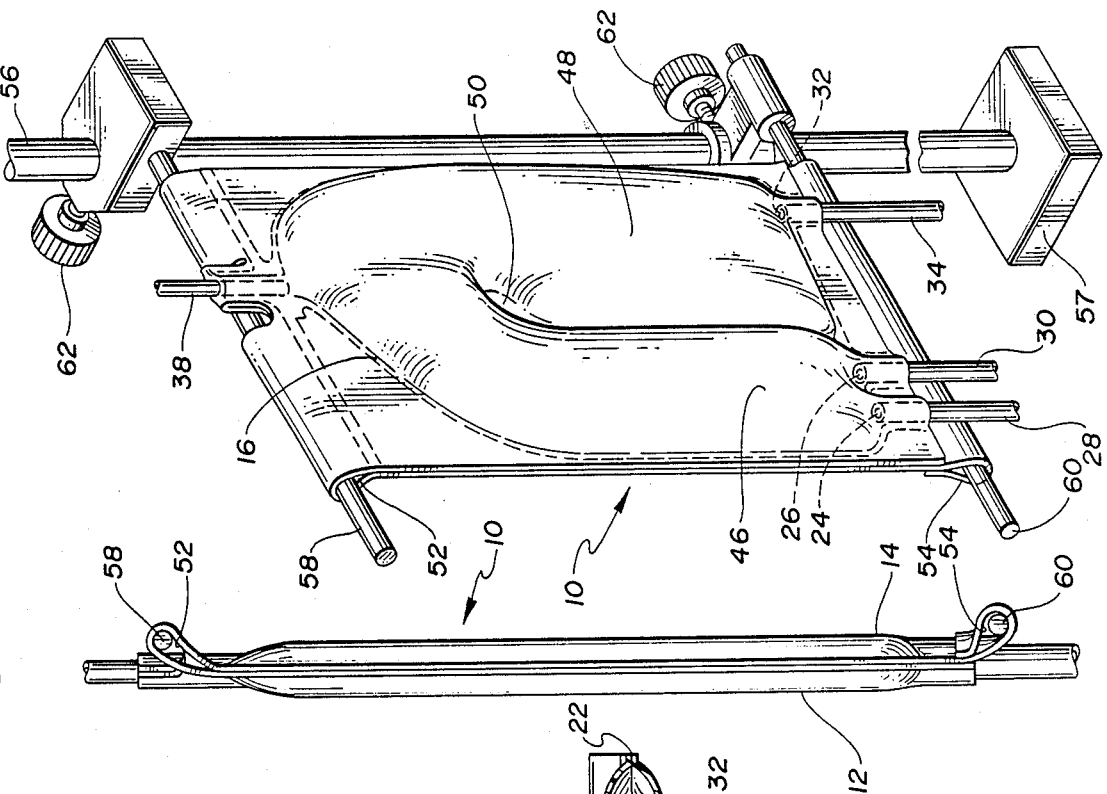
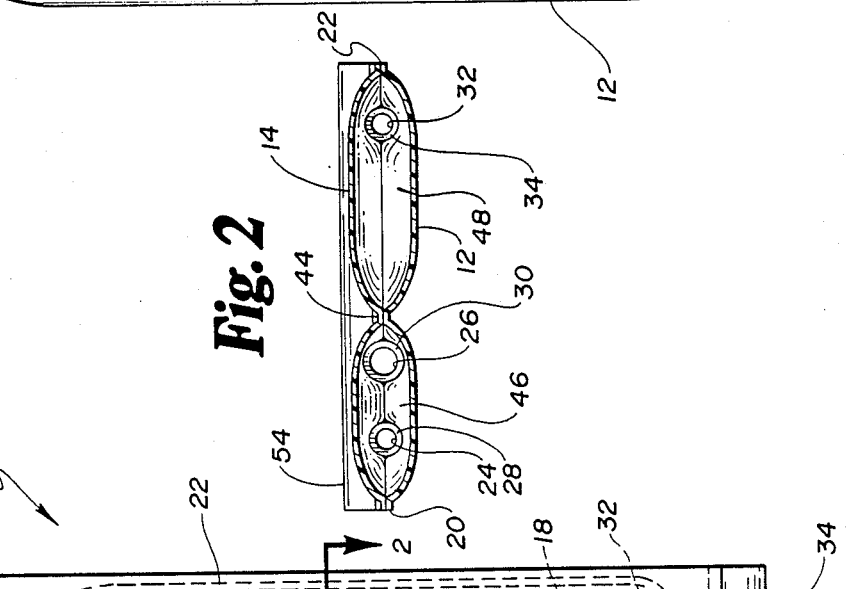
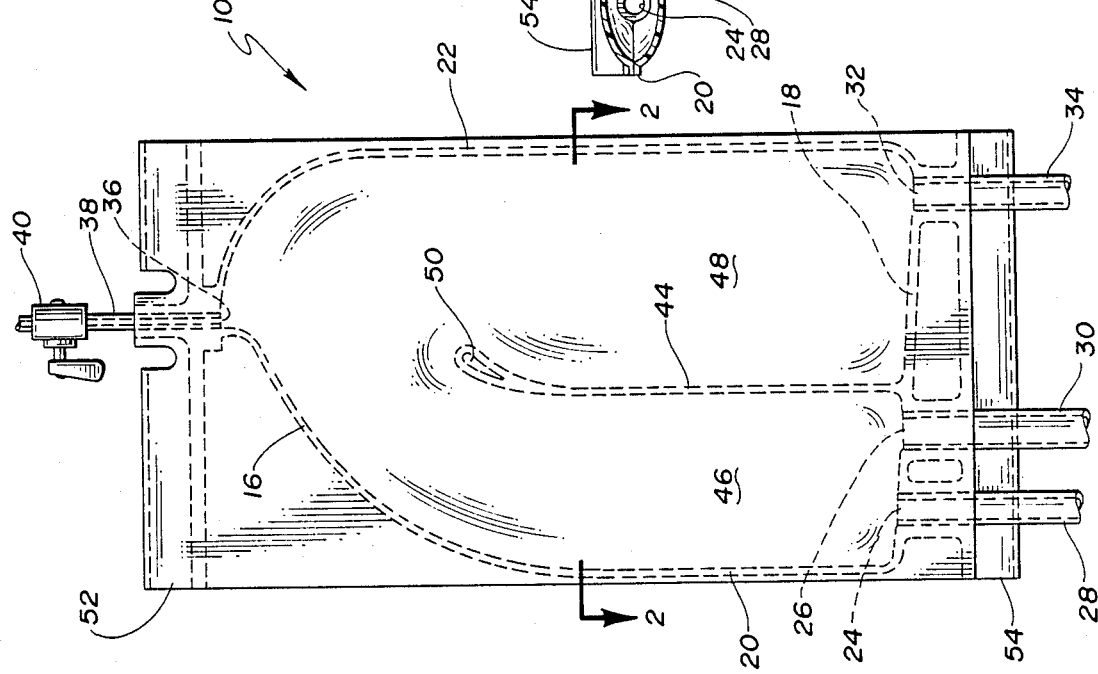

VENOUS RESERVOIR

DESCRIPTION

1. Field of the Invention

This invention relates to a venous reservoir for use in clinical cardiopulminary bypasses.

2. Background of the Invention

Cardiopulminarv bypasses involve a diversion of the flow of blood from the entrance of the right atrium to an extracorporeal blood circuit. Such circuits typically include some form of blood oxygenator, a pump, warning instrumentation, cardiotomy reservoir and venous reservoir.

Such reservoirs involve the storage of priming solution and contain excess fluid as a result of patient volume changes as well as acting as bubble traps. Collapsible reservoirs will collapse if accidently pumped dry to prevent the entry of air into the oxygenator system which may form air embolisms in patients.

Typical flexible, collapsible venous reservoirs are formed by sealing two plastic sheets together such that a volume is defined therewithin. The Capiox II brand venous reservoir of Terumo Corporation is a typical reservoir bag in which the cardiotomy inlet and venous inlet enter the bottom of the reservoir bag as standpipes and the bag is emptied by a lower outlet in the same chamber. Venting is supplied by a number of valve controlled ports. Such standpipes are undesirable. Standpipes prevent the bag from fully collapsing and may allow air to be pumped into a patient. Also, the standpipes create areas of stagnant blood below the outlets of the pipes in which thrombosis may occur.

A Bentley brand venous reservoir of American Hospital Supply Corporation of Irvine, Calif., eliminates the use of standpipes in its bladder-shaped flexible reservoir. The single chambered reservoir employs a single combined inlet for the cardiotomy reservoir and venous blood. An upper vent allows trapped air bubbles to escape. A lower outlet on the other side of the bag empties the reservoir.

In U.S. Pat. No 4,026,669 to Leonard et al, a variable capacity venous reservoir is described in which the volume may be varied by the use of a single, bifurcated metal clamp which grasps the reservoir between the inlets and outlets. The clamp is slidable upwardly and downwardly so as to permit volume control over a predetermined range. The positioning between the main blood inlet and main blood outlet enhances the reservoir bubble trap effect by directing blood and bubbles upwardly toward a vent.

It is an object of this invention to provide a collapsible reservoir which is collapsed completely when pumped dry so as to prevent the introduction of air into the patient. It is a further object of the invention to provide a venous reservoir in which the opposing walls are sealed theretogether from the bottom seal upwardly between the inlets and outlets so as to define a blood inlet chamber and blood outlet chamber which communicate with each other at the top of a vertical seal. The vertical seal provides volume control and enhances the removal of bubbles from blood within the reservoir.

It is a still further object of the invention to construction the reservoir such that the inlets and outlets provide no internal standpipes in order to minimize thrombosis.

BRIEF SUMMARY OF THE INVENTION

The venous reservoir of the invention comprises a pair of flat, flexible plastic sheets which are joined together by heat or electronic weld-type sealing along their periphery so as to define a reservoir chamber therebetween. The seal lines are formed generally at the top, side and bottom edges of the plastic sheets. At least one venous blood inlet enters the bottom of the venous reservoir and at least one venous blood outlet exit the bottom of the reservoir. All inlets and outlets are constructed and arranged by sealing the two facing plastic sheets over inlet and outlet tubing whose tubing ends do not extend within the cavity defined by the plastic seals. In this manner, no standpipes are formed and areas of stagnant blood flow are minimized to decrease the possibility of thrombosis or blood stagnation in the areas of the tubing inlet and outlet.

The top seal is perforated by a valve controlled vent so as to allow the aspiration of air from the reservoir, and the addition of medications used during (CPB).

The two plastic sheets forming the reservoir are additionally welded together from the bottom seat and extending upwardly toward, but not reaching, the top seal such that a barrier is provided within the reservoir. The vertical seal is provided between the outlets and inlets such that all venous blood must flow upwardly past the top of the barrier before flowing downwardly towards the outlet. In this manner, blood, with its entrapped bubbles, is directed upwardly towards the aspiration vent. As the blood descends toward the blood outlet chamber, the bubbles are free to rise toward the top of the reservoir where they may be removed by aspiration. It has been found that by spacing the vertical barrier seal such that the chamber defined between the barrier and the side seal adjacent the inlets is narrower than the blood outlet chamber defined by the barrier and the side seal adjacent the blood outlet enhances the removal of bubbles from the blood. The narrower blood path maintains a relatively high velocity of blood flow on the blood inlet side which suddenly decreases after passing the top of the barrier seal. It has been found that the sudden, marked reduction of blood flow rate (or velocity) tends to increase the removal of bubbles from the blood.

Preferably, the barrier seal extends upwardly and curves toward the blood outlet chamber in order to further direct blood toward the blood outlet chamber. Also, it is desirable for the blood inlet chamber side seal to curve towards the top of the reservoir and towards the blood outlet chamber so as to direct blood upwardly and toward the blood outlet chamber.

The volume of the venous reservoir of the invention may be controlled by a unique bilateral suspension. One sheet forming the venous reservoir is preferably longer at the top and bottom edges such that it may be looped over and sealed at each end to form rod passage holes. The mounting system comprises a vertical stand to which a pair of horizontal, parallel rod members are slidably attached. Each rod is passed through the rod passageway of the venous reservoir and the tautness of the reservoir, which is determined by the separation of the horizontal rods, determines the maximum volume of the venous reservoir. When the rods are spaced apart as far as possible the venous reservoir will not be allowed to expand to its full potential. Conversely, when the horizontal rods are closer together the venous reservoir bag is allowed to expand outwardly such that a higher volume of blood is obtainable within the bag.

BRIEF DESCRIPTION OF THE DRAWINGS

A detailed description of the invention is hereafter described with the specified reference being made to the drawings in which:

FIG. 1 is a front view of the venous reservoir of the invention;

FIG. 2 is a cross sectional view taken at line 2—2 of FIG. 1;

FIG. 3 is a side view showing the venous reservoir hung between two rod supports; and FIG. 4 is perspective view of the venous reservoir hung from an adjustable stand.

DETAILED DESCRIPTION OF THE INVENTION

Referring to the drawings, the venous reservoir 10 shown in FIGS. 1–4 is made of a flexible plastic material, preferably polyvinylchloride. The reservoir 10 is comprised of a front sheet 12 and rear sheet 14 sealed along the top edge 16, bottom edge 18 and side edges 20 and 22 by electronic welding or other suitable means to form a permanent, liquid-tight seal.

A pair of blood inlet ports 24 and 26 are provided extending through the sealed bottom edge 18 to provide access to the reservoir. Ports 24 and 26 are preferably formed by positioning tubing 28 and 30 between sheets 12 and 14 before sealing. The bottom edge seal 18 is then formed and preferably extends completely around the circumference of the tubing for at least ½". As shown in FIG. 1, tubing 28 and 30 do not extend past seal line 18 and thereby present no projection into the interior of the venous reservoir defined by the edge seals.

In a like manner, the outlet port 32 is formed by sealing tubing 34 to bottom edge seal 18 as described above for the blood inlet ports. Again, no portion of tubing 34 extends into the venous reservoir defined by the edge seals.

An aspiration vent port 36 is provided which extends through sealed top edge 16 to provide access to the container. Vent port 36 includes tubing 38 which is sealed between front and rear sheets 12 and 14 as shown. Preferably, tubing 38 does not extend into the cavity defined by seals 16, 18, 20, and 22. However, since blood is less likely to be present around tubing 38, the chances of thrombosis occurring around tubing 38 if it extends slightly within venous reservoir 10 is much less than if tubing 28, 30 or 34 were to extend into venous reservoir cavity 10. Tubing 38 is provided with a finger controlled valve such that venous reservoir 10 may be aspirated by opening normally closed valve 40.

As best shown in FIG. 1, side seal 20 is relatively straight along the lower half of the reservoir at which point it begins to curve toward the top edge seal 16 and side edge seal 22. This tends to direct blood from the inlets upwardly toward vent 36.

A vertical seal line is also provided between sheet 12 and 14, as shown, extending from bottom edge seal 18 upwardly toward top edge seal 16. Vertical seal line 44 defines a blood inlet chamber 46 and blood outlet chamber 48. The uppermost portion of vertical seal line 44 is preferably made as shown in FIG. 1 to include a double seal for strength and to form a rounded end 50 which curves toward edge seal 22 as shown. Vertical seal line 44 is placed between blood inlets 24, 26 and blood outlet 32 so as to define chambers 46 and 48. It has been found that forming vertical seal line 44 closer to seal line 20 than seal line 22 causes blood within blood inlet chamber 46 to flow at a substantially higher velocity than blood within chamber 48. This increases the removal of bubbles from the blood within the venous reservoir. As blood within inlet chamber 46 passes rounded end 50, it enters the relatively large blood outlet chamber 48 and decreases in velocity. This decrease in velocity, aided with the differing effects of gravity on blood and bubbles, increases the clearance of bubbles from the blood. The bubbles collect in the uppermost portion of reservoir 10 and are vented through port 36 by opening valve 40. The possibility of an air embolism occurring is thereby reduced by the use of the novel venous reservoir due to its bubble clearing properties.

In order to control the volume of venous reservoir 10, the reservoir bag is held in a bilateral suspension. The rear sheet 14 is longer than front sheet 12 such that excess plastic remains at the top and bottom edges after forming seals 16 and 18. The excess plastic on each end of sheet 14 is then looped over as shown in FIGS. 2 and 3 and sealed to form rod passage holes 52 and 54.

The mounting system comprises a vertical rod 56 mounted to a base 57 as shown, to which a pair of horizontal, parallel rod members 58 and 60 are slidably attached. Preferably, rod members 58 and 60 include set screws 62 which may be loosened and tightened readily to allow the rod members to be repositioned at will.

Rod members 58 and 60 are passed through rod passage holes 52 and 54 respectively of venous reservoir 10. The tautness of the reservoir is determined by the separation between horizontal rod members 58 and 60. The tautness itself determines the maximum volume of the venous reservoir. When the rods are spaced as far apart as possible, the venous reservoir will have a relatively small volume. Conversely, if the reservoir bag 10 is held relatively loosely between horizontal rod members 58 and 60, sheets 12 and 14 will be allowed to expand outwardly such that a higher volume of blood is obtainable within reservoir 10. In this manner, the priming volume of venous reservoir 10 may be changed at any time during the oxygenation procedure of a patient by merely adjusting one or both of the horizontal rod members.

In considering this invention it must be remembered that the disclosure is illustrative on)y and that the scope of the invention is to be determined by the appended claims.

What is claimed is:

1. A method of varying the volume of a blood reservoir, the blood reservoir of the type comprising:
   (a) front and rear plastic sheets sealingly joined together at their respective top, side and bottom edges so as to define a liquid-tight blood reservoir chamber therebetween;
   (b) at least one blood inlet on the bottom edge of said blood reservoir communicating with said blood reservoir chamber for directing blood flow into said blood reservoir chamber;
   (c) at least one blood outlet on the bottom edge of said blood reservoir communicating with said blood reservoir chamber for directing blood flow from said blood reservoir chamber;
   (d) vent means for venting said blood reservoir chamber, said vent means communicating with said reservoir chamber at the top edge of said reservoir;

(e) barrier means comprised of a seal line between said front and rear sheets extending from the bottom edge of said reservoir between said inlets and outlets, and extending upwardly toward between said inlets and outlets, and extending upwardly toward but not reaching said top edge of said reservoir such that an inlet chamber is defined on the side of said inlets and an outlet chamber is defined on the side of said outlets;

(f) said reservoir being constructed and arranged such that one of said sheets is extended in length and said extended sheet is looped at the top and bottom and sealed so as to form rod passage ways on the top and bottom outer edges of said reservoir such that said reservoir may be mounted to a bracket assembly having a vertical support to which horizontal, parallel rod members are attached so as to allow one or both rod members to move upwardly or downwardly on said vertical support, such that when said venous reservoir rod passageways are positioned over said parallel rod members, said reservoirs are fixedly held in a position for use, and tension applied by moving one horizontal rod member away from the other decreases the maximum volume obtainable within said reservoir;

(g) said method comprising the steps of (a) hanging the reservoir on a bracket assembly such that a horizontal rod members passes through said top and bottom loops of said reservoir and (b) varying the distance between said horizontal rod members when said reservoir is held therebetween so as to alter the maximum volume obtainable within said reservoir.

* * * * *